United States Patent [19]
Logan et al.

[11] Patent Number: 6,017,525
[45] Date of Patent: Jan. 25, 2000

[54] POULTRY HOUSE LITTER TREATMENT

[76] Inventors: Walter T. Logan, Postal Rte. 1, Box 160, Buena Vista, Va. 24416; Stephen L. Bartlett, 5310 Cendronella Rd., Chapel Hill, N.C. 27514

[21] Appl. No.: 09/050,842

[22] Filed: Mar. 30, 1998

Related U.S. Application Data

[60] Provisional application No. 60/042,600, Apr. 2, 1997.

[51] Int. Cl.[7] ............................. A01N 63/00; C12N 1/20; A01K 29/00
[52] U.S. Cl. ..................................... 424/93.46; 435/252.5; 435/834; 119/171
[58] Field of Search ................................ 424/93.46, 76.1, 424/76.5; 119/171

[56] References Cited

U.S. PATENT DOCUMENTS

| | | | |
|---|---|---|---|
| 3,808,102 | 4/1974 | Douros et al. | 435/252.31 |
| 4,218,233 | 8/1980 | Hackett . | |
| 4,284,722 | 8/1981 | Tamuri et al. | 435/94 |
| 4,311,115 | 1/1982 | Litzinger | 119/1 |
| 4,511,552 | 4/1985 | Cox . | |
| 4,695,462 | 9/1987 | Barnes et al. | 424/195.1 |
| 4,999,193 | 3/1991 | Nguyen | 424/93 |
| 5,154,594 | 10/1992 | Gamlen | 119/171 |
| 5,252,329 | 10/1993 | Nuotio et al. . | |
| 5,451,400 | 9/1995 | Stern et al. . | |
| 5,478,557 | 12/1995 | Nisbet . | |
| 5,604,127 | 2/1997 | Nisbet . | |

FOREIGN PATENT DOCUMENTS 7-222791   8/1995   Japan .

*Primary Examiner*—Sandra E. Saucier
*Assistant Examiner*—Vera Afremova
*Attorney, Agent, or Firm*—Donavon Lee Favre

[57] ABSTRACT

A dry composition containing large numbers of beneficial bacteria and enzymes for the digestion of poultry manure is used to treat poultry litter. The growth of the beneficial bacteria, activated by moisture in poultry droppings prevents the growth of pathogenic bacteria such as *E. coli*, Salmonella and Campylobacter by competitive exclusion.

14 Claims, No Drawings

POULTRY HOUSE LITTER TREATMENT

CROSS-REFERENCE TO RELATED APPLICATIONS

Applicants hereby claim the benefit of Provisional Application No. 60/042600 filed Apr. 2, 1997 entitled POULTRY HOUSE LITTER TREATMENT, naming the same inventors as the present application.

STATEMENT REGARDING FEDERALLY SPONSORED RESEARCH OR DEVELOPMENT

Not Applicable

BACKGROUND OF THE INVENTION

1. Field of the Invention

The present invention is directed to a dry mixture of bacteria and enzyme used in poultry house litter treatment floor ammonia control and increased growout productivity of the poultry.

2. Background of the Invention

Poultry house litter is treated with acidic material which neutralize basic ammonium compound to prevent the release of ammonia. While useful for the intended purpose, acidic materials have harmful side effects.

To eliminate the harmful side effects, the present inventors developed a bacteria-enzyme mixture that is suspended in water and sprayed onto the chicken litter at frequent intervals to digest the ammonia compounds and reduce the ammonia emissions. The composition of the liquid product is a trade secret.

U.S. Pat. No. 4,218,233 Hackett (1980) discloses a method for reducing offensive odors in poultry houses by adding at least ten pounds cow manure composed with thermophilic aerobic bacteria per ton of poultry manure in manure pits below chicken cages. The composted cow manure can have a moisture content of 20–30% to produce a material which itself can be composted by aerobic thermophilic bacteria at pasteurizing temperatures.

U.S. Pat. No. 4,511,552 Cox (1985) discloses at claims 24, 25 and 26 a lagoon-conditioning floater carrying a biodegradant. The biodegradant is one or more selected from the class of bacteria, fungi, and enzymes. The bacteria can be for example *Strepiococciis fecealis* and/or *Strepoccus diacetylactis*

U.S. Pat. No. 5,252,329 Nuotio (19931) discloses a bacterial preparation useful for the prophylaxis of intestinal bacterial infections, especially Campylobacitel infections, in poultry. The preparation contains bacteria derived from an adult bird from the same microecological niche, especially in the caecum, where the pathogenic bacteria tend to propagate in newly hatched chickens.

U.S. Pat. No. 5,451,400 Stern et al (1995) discloses a preparation for reducing colonization by human enteropathogenic bacteria in poultry prepared from cultures of mucosa-associated flora obtained from ceca of mature birds and is referred to as mucosal competitive exclusion (MCE). The preparation is especially effective for both Samonella and Campylobacter spp.

U.S. Pat. No. 5,478,557 Nisbet et al (1995) discloses a defined probiotic or composition of anaerobic bacteria effective for controlling or inhibiting Samonella colonization of fowl. The probiotic includes populations or cultures of 29 substantially biologically pure bacteria. In use, the probiotic is administered to the subject fowl in an amount effective for increasing resistance to Samonella colonization thereof U.S. Pat. No. 5,604,127 Nisbet et al (1997) discloses a defined probiotic or composition of anaerobic bacteria effective for controllilng or inhibiting Salmonella colonization of fowl. The probiotic includes populations or cultures of substantially biologically pure bacteria, which bacteria include at least one species of Lcatcohacillhs, one or both of *Laclococcils lactis*, and *Citrobacter freundii*; and at least one of
one or more Enteroccus species,
one or more Bifidobacterium species, and
one or more Propionibacterium species, and
one or more Escherichia species.

BRIEF SUMMARY OF THE INVENTION

The present invention is directed to a bacteria-enzyme composition comprising a dry mixture of fast growling bacteria that are not harmful to humans, a protease enzyme, and nutrients for the bacteria. The bacteria-enzyme composition is formulated to be applied dry at the beginning of a poultry growout and provides benefits for one entire growout cycle. The bacteria-enzyme composition is usually applied at a minimum rate of $1.5 \times 10^9$ bacteria per square foot just prior to placement of new birds and after disinfection. The upper limit is not critical and is governed primarily by cost. The nutrients in bacteria-enzyme composition can include sugar and citric acid. A buffer such sodium bicarbonate is also preferably present.

The bacteria are activated by the moisture in the poultry droppings.

The bacteria-enzyme composition of the present invention when used to treat poultry house litter introduces massive numbers of harmless bacteria, adept at the degradation of organic wastes, in this case poultry manure reducing the ammonia levels in the poultry house. Ammonia in abundance results when urea is converted to ammonia at a faster rate than ammonia is converted to nitrite. The reduction of ammonia levels improves growout performance by reducing environmental stresses on poultry. In addition to the reduction of ammonia, the massive population of beneficial bacteria grown from the bacteria-enzyme composition crowd out other opportunistic microbes and maintain an artificially high population shift in favor of the bacteria in the bacteria-enzyme composition. This action is called competitive exclusion and further reduces the birds' immunological stress. Gut binding sites are inhabited by the harmless organisms seeded by the bacteria-enzyme composition and the birds experience a lowered immunological challenge. Stastically, birds are less likely to pick up potentially harmful microbes when pecking in litter because so many of the microbes present are harmless bacteria-enzymiie composition microbes. The result is healthier, less immunologically stressed poultry that respond with better feed utilization, weight gain and livability.

The bacteria-enzyme composition of the present invention uses naturally occurring bacteria to improve poultry growout house environments by reducing ammonia, composting manure, and shifting microbial populations toward high densities of harmless bacteria.

The concentration of birds per area, for example 25,000 birds growing, in the confines of a 16,000–20,000 square foot house create volumes of waste that simply overwhelm Nature's ability to process it. The bacteria-enzyme composition concentrates Nature's own waste degrading microorganisms in poultry litter to assist in this natural process. The bacteria-enzyme composition attacks the cause of the ammonia biochemically. These are the same types of microorganisms used by nature to recycle carbon and nitrogen within the environment. As these naturaliy occurrinlg bacteria utilize the nutrients in chicken manure to grow and reproduce, the amount of ammonia produced is lowered.

It has been well documented that high levels of ammonia caused by decomposing manure stress birds. Unhealthy birds cost growers lost profits in higher mortalities, lower weights and poorer feed conversion.

One application of the bacteria-enzyme composition of the present invention maintains the reduction of ammonia for the entire growout cycle. The chemical litter amendments of the prior art such as sodium hydrogen sulfate and mono-calcium phosphate are actually dry acids or binders that work by reducing the litter's pH to hold ammonia in a liquid, non-gaseous state, or bind the components of ammonia. They require the distribution of several hundred pounds of chemicals and are corrosive. These chemicals are soon neutralized by the increasing amounts of waste generated. Within a week or two, ammonia levels begin to climb and remain uncontrolled for the rest of a growout. This results in 4 to 6 weeks of exposure to higher ammonia levels for birds and growers alike.

With the dry bacteria-enzyme composition of the present invention ammonia is reduced for an entire growout cycle, and the incidence of late cycle mortality has been shown to be reduced by as much as 23%. It is applied at the rate of approximately one pound per 1,000 square feet just prior to placement of new birds and after disinfection. Preferably an application of a liquid suspension of the bacteria and enzymes of the composition is also used to initiate the culture of non-pathogenic bacteria in the litter prior to the application of the dry composition. The concentration of enzyme(s) is higher in the liquid suspension to accelerated the digestion of any residual waste and to aid in the replacement of residual pathogenic bacteria.

Far more investment is lost when birds die late in the cycle. The bacteria-enzyme composition can be applied while birds are in the house, so that the grower has the advantage of maintaining control in times of stress. The present invention does not require the spreading of hundreds of pounds of ammonia neutralizer as does the prior art. An average chicken house can be treated for an entire growout with 20 pounds. In addition the bacteria-enzyme composition of the present invention is not corrosive to equipment or poultry house fixtures.

Continued use of the bacteria-enzymiie composition of the present invention will actually condition litter by composting it in place, allowing longer use of floor litter between clean outs. In a recent test, houses that had been used for trial in 5 consecutive growout were tested for ammonia by digging down to floor level and taking samples. Ammonia in the treated houses averaged 10–12 ppm in the litter, while the untreated houses averaged over 100 ppm.

The longer the bacteria-enzyme composition of the present invention used, the better its results in productivity improvement become. The bacteria-enzyme composition is entirely safe to use on litter that will be added to animal feed, spread as fertilizer or used in mushroom culture. The nitrogen stabilization process of the microbial activity of the present invention actually produces a higher fertilizer value in the litter.

To be more specific, the dry composition or the present invention for use in treating poultry litter to prevent the growth of pathogenic bacteria contains high concentrations of one or more non pathogenic bacteria, which bacteria because of their shear numbers and growth rate overwhelm pathogenic bacteria in the litter. The inventive composition also contains one or more enzymes capable of breaking down the manure for digestion by the noni-patlhogenic bacteria, and a particulate absorbent carrier for the bacteria and the enzymes, the carrier having major and minor dimensions each greater than 2 millimeters.

The bacteria of the present invention are preferably selected from the class comprising *Bacillus cereus, Bacillus lentimorbus*, and *Bacillus stearothermophilus* and mixtures thereof. The enzyme is preferably selected from the class comprising protease, amylase, and lipase and mixtures thereof. The carrier is preferably perlite.

A method of the present invention is directed to the treatment of poultry litter, deposited for the collection of manure, to prevent the growth of pathogenic bacteria in the litter. In the practice of the method a dry composition containing one or more non pathogenic bacteria, which bacteria grow faster on poultry manure than pathogenic bacteria and one or more enzymes capable of breaking down the manure for digestion by the bacteria are applied to the litter. The bacteria and enzymes are activated by the moisture in subsequently dropped mianiure over the period of time corresponding to a poultry growout cycle. By "grow faster" is meant that the non-pathogenic bacteria by shear numbers simply overwhelm the pathogenic bacteria.

The bacteria and enzymes are preferably carried on a particulate absorbent carrier for the bacteria and the enzymes. The carrier preferably has major and minor dimensions each greater than 2 millimeters and less than 1 centimeter. The size is such that the composition of the present invention can be uniformly distributed over the surface of the litter by a spreader normally used to broadcast seed 7. The bacteria are preferably selected from the class comprising *Bacillus cereus, Bacillus lentimorbus*, and *Bacillus stearothermophilus* and mixtures thereof. The enzyme is preferably selected from the class comprising protease, amylase, lipase and mixtures thereof. The carrier is preferably an absorbent organic or inorganic material, one specific embodiment being perlite. The bacteria are deposited at a concentration of greater than $1\times10^8$ bacteria per square foot of litter. Preferably the bacteria are deposited at a concentration of from a small but effective amount to prevent the growth of pathogenic bacteria to an amount equal to or greater than $1.5\times10^9$ bacteria per square foot of litter.

BRIEF DESCRIPTION OF THE SEVERAL VIEWS OF THE DRAWING

Not Applicable

DETAILED DESCRIPTION OF THE INVENTION

The composition of IMPACT-P environmental control used in the following examples is as follows:

| | | |
|---|---|---|
| NAS-1, a mixture of *Bacillus lentimorbus* strains and *Bacillus stearothermophilus* strains | 6% (available from Ryter Labs) | 9 lb./150 lb. |
| NAS-5, same as NAS-1 plus amylase and lipase enzymes | 10% | 15 lb./150 lb. |
| Dynabac 1000, *Bacillus cereus*. (from Nugen Inc.) | 1.34% | 2 lb/150 lb |
| Hubersorb | 1.67% | 2.5 lb/150 lb |
| sugar | 10% | 15 lb/150 lb |
| sodium bicarbonate | 21.34% | 32 lb/150 lb |
| protease enzyme (AP Gran.)[8] | 24.67% having 450,000 casein digestive units | 37 lb/150 lb |
| Perlite | 25% | 37.5 lb/150 lb |

The composition also contains a citrate on the order of 7 pounds/150 pounds of product. The enzyme is preferably present at a level of from a small but sufficient amount to reduce ammonia gas production to a level of 450,000 casein digestive units. Preferability less than 40% by weight of enzyme is present in the product.

In the following tables Air Sac % refers to Saculitis, Sept/Tox % refers to Septicemia Toxicicity, Hubersorb is a dessicant, F/C refers to feed conversion. Two successive growout were used to evaluate need activated IMPACT-P® enviromental control in chichen houses. There were some minor errors in chichen counts. The workers who catch chickens were paid by the number of chickens that they caught. When the numbers of surviving chickens exceeded 100%, the calculations were based upon 100% survival. The errors in chicken counts were just as likely to occur with the control as with the IMPACT-P-treated houses The houses were reversed for the second growout. In both trials the need activated IMPACT-P treated houses out performed the untreated house. Over the 2 grow outs the houses treated with need activated IMPACT-P returned 0.855 cents per lb. more settlement pay to the grower than the untreated houses. The results are set forth in the following table:

|  | Net lbs. produced | pay per lb. | settlement |
|---|---|---|---|
| need activated IMPACT-P treated | 292,305 | .04435 | $12,963.73 |
| Untreated | 283,732 | .03580 | $10,157.61 |
| Variance | 8,573 | .00855 | $2,806.12 |

The cost of the need activated IMPACT-P, used to treat for 2 flocks was $462.50 (50 lbs). The product was applied at the recommended rate of 1 lb. per 1,000 square feet of floor area. These houses were cleaned out an new litter added before each trial.

The return rate to the grower for these trails was $6.07 per $1.00 of cost. Fuel savings were also reported by the grower. Adjusted for historical differences in consumption, the grower saved $275 in the first growout and $300 in the second growout in the houses using need activated IMPACT-P.

Condemnation data provides evidence that need activated IMPACT-P improves air quality and competitively excludes potentially harmful microbes in floor litter.

| House | growout | Status | Competitive Exclusion Sept/Tox % | Air Quality Air Sac % |
|---|---|---|---|---|
| #1 | 3/8/96–4/19/96 | control | .22 | .30 |
| #1 | 4/29/96–6/12/96 | IMPACT-P | .16 | .01 |
| #2 | 4/29/96–6/13/96 | control | .24 | .09 |
| #2 | 3/8/96–4/19/96 | IMPACT-P | .11 | .06 |

It is also noteworthy that although a major advantage of need activated IMPACT-P is ammonia reduction, the second of these trials was conducted in mild weather providing further evidence that the need activated IMPACT-P litter treatment effects significant production improvment even when broiler houseds are open and well ventilated.

Other Results form the March-June, 1996 Tests trial 3/8/96 to 4/19/96

| House # | Age in days | Average weight | Living % | Adjusted Food/Conversion | Condemned | Pay/Pound |
|---|---|---|---|---|---|---|
| #1, no IMPACT-P | 42 | 3.80 | 94.98 | 2.09 | .73 | 3.11 |
| #2, with IMPACT-P | 42 | 3.99 | 96.93 | 1.97 | .33 | 3.74 |
| Variance |  | +.19 | +1.95 | (.12) | (.40) | +0.63 | trial 4/29/96 to 6/13/96

| House # | Age in days | Average weight | Living % | Adjusted Food/Conversion | Condemned | Pay/Pound |
|---|---|---|---|---|---|---|
| #2, no IMPACT-P | 44 | 4.43 | 96.24 | 1.92 | .71 | 4.05 |
| #1, With IMPACT-P | 43 | 4.33 | 96.69 | 1.86 | .31 | 5.13 |
| Variance | (1) | (.10) | +.45 | (.06) | (.40) | +1.08 |

House #1 Trials 3/8/96 to 4/19/96 vs 4/29/96 to 6/12/96

| House #1 | Age | Average Weight | Living % | Adjusted Food/Conversion | Condemned | Pay/Pound |
|---|---|---|---|---|---|---|
| 4/96 no IMPACT-P | 42 | 3.80 | 94.98 | 2.09 | .73 | 3.11 |
| 6/96 with IMPACT-P | 43 | 4.33 | 96.69 | 1.86 | .31 | 5.13 |
| Variance | +1 | +.53 | +1.71 | (.23) | (.42) | +2.02 |

House #2 trials 3/8/96 to 4/19/96 vs 4/29/96 to 6/13/96

| House #2 | Age | Average Weight | Living % | Adjusted Food/Conversion | Condemned | Pay/Pound |
|---|---|---|---|---|---|---|
| 4/96 no IMPACT-P | 44 | 4.43 | 96.24 | 1.92 | .33 | 4.05 |
| 6/96 with IMPACT-P | 42 | 3.99 | 96.93 | 1.97 | .71 | 3.74 |
| Variance | (2) | (.44) | +.69 | +.05 | (.38) | (.31) |

In this evaluation the Integrator reversed the houses for the second growout trial, treating what had been used as the control house with need activated IMPACT-P and using the house that was treated with IMPACT-P in the first growout as an untreated control. In both trials the IMPACT-P treated house outperformed the untreated house. Over the two grow outs the houses treated with IMPACT-P returned 8.55 cents per pound more settlement pay to the grower than the untreated houses.

|  | Net pounds produced | pay per pound | settlement |
|---|---|---|---|
| IMPACT-P treated | 292,305 | .04435 | $12,963.73 |
| Untreated | 283,732 | .03580 | $10.157.61 |
| Variance | 8,773 | .00855 | $2,806.12 |

Cost of need activated IMPACT-P used to treat for two flocks=$462.50 (50 pounds). The product was applied at the recommended rate of one pound per 1,000 square feet of floor area after new litter was added. These houses were cleaned out and new litter added before each trial. The return rate to the grower for these trials was $6.07 per $1.00 of cost. Fuel savings were also reported by the grower. Adjusted for historical differences in consumption the grower saved $275.00 in the first growout and $300.00 in the second growout in the houses using need activated IMPACT-P. The integrator relized an increase in net pounds from birds started of 8,573 pounds or 3%, and the cost to produce using need activated IMPACT-P was also significantly less in both trials, by 1.37 cents per pound and 1.08 cents per pound respectively

| Trial #1 | cents per pound | Trial #2 | cents per pound |
|---|---|---|---|
| Control | 28.63 | Control | 30.44 |
| need activated IMPACT-P | 27.26 | need activated IMPACT-P | 29.36 |
| Variance | 1.37 | Variance | 1.08 |

The used need activated IMPACT-P poultry litter treatment results both in an improvement of air quality by ammonia reduction and a reduction in immunological stress from populations in the floor litter by competitive exclusion. The artificially high populations of IMPACT-P bacteria excludes potentially harmful microbes. Looking at the condemnation data from these studies provides support for both claims.

| House | growout | Status | Competitive Inhibition Sept/Tox % | Air Quality Air Sac % |
|---|---|---|---|---|
| #1 | 3/8/96–4/19/96 | control | .22 | .30 |
| #1 | 4/29/96–6/12/96 | need activated IMPACT-P | .16 | .01 |
| #2 | 4/29/96–6/13/96 | control | .24 | .09 |
| #2 | 3/8/96–4/19/96 | need activated IMPACT-P | .11 | .06 |

It is also noteworthy that although a major advantage of need activated IMPACT-P litter treatment is ammonia reduction, the second of these trials was conducted in mild weather providing further evidence that the need activated IMPACT-P litter treatment effects significant production improvement even when broiler houses are open and well ventilated.

Two farms managed by the same grower and receiving flocks during the same week were used to test need activated IMPACT-P poultry litter treatment. Need activated IMPACT-P is a dry formula which is activated by the moisture in poultry droppings. The performance of need activated IMPACT-P was established for two consecutive growout. BLR is a 4 house, 55,000 square foot farm and PLR is a 2 house 30,000 square foot farm. PLR was treated with need activated IMPACT-P at 1 pound per 1,000 square feet. Total pound required for each growout: House #1, 12 pounds and house #2, 18 pounds. The Results are set forth in the following table.

| Growout February 9, 1996–March 27, 1996 | | | | | |
|---|---|---|---|---|---|
| | Age | LIV % | average weight | F/C | Condemned % | Rank |
| BLR | 46 | 994 | 4.03 | 1.997 | .44 | 14/15 |
| PLR | 43 | 100 | 3.94 | 1.89 | .25 | 3/12 |

Grower pay per 1,000 birds started: (PLR 44,000; BLR 88,600)

PLR=$162.13; BLR=135.32; Variance=$26.81

| Growout April 22, 1996–June 7, 1996 | | | | | |
|---|---|---|---|---|---|
| | Age | LIV % | Average Weight | F/C | Condemned % | Rank |
| BRL | 43 | 100 | 3.78 | 1.94 | .15 | n/a |
| PRL | 45 | 100 | 3.85 | 1.93 | .19 | n/a |

Grower pay per 1,000 birds started: (PLR 43,700; BLR 81,200)

PLR=$134.33; BLR=$118.43; Variance=$15.90

Discussion: In the February-March growout if needed activated IMPACT-P litter treatment had been used on BLR this grower could have expected to earn an additional $2,375.36 ($26.81×88.6). In the April-June growout need activated IMPACT-P litter treatment of BLR could have returned an additional $1,291.08 ($15.90×81.2)

houses was 29% higher. The return on investment was $4.15 per $1.00 product cost.

SAME FARM, MATCHED HOUSE TRIALS-SAME BREED PLACED ON THE SAME DAY

|  | Living | Gain/Day | Food Conversion | Condemned | Saculitis | % Grade A Paws | % Grade B Paws |
|---|---|---|---|---|---|---|---|
| Average Test | 96.99 | 1000 | 1.91 | 0.75 | 0.08 | 54.38 | 22.38 |
| Average Control | 96.72 | 994 | 1.93 | 0.93 | 0.14 | 41.08 | 23.74 |
| ABOVE COMPARED TO 7 FLOCK HISTORIES |  |  |  |  |  |  |  |
|  | 97.26 | 997 | 1.91 | 0.62 | 0.06 | 43.27 | 26.28 |

|  | Growout #1 | Growout #2 | Total |
|---|---|---|---|
| Gain Possible | $2,395.36 | $1,291.08 | $3,666.44 |
| Added Cost of IMPACT-P | $508.75 | $508.75 | $1,017.50 |
| Net Gain $ | $1,866.61 | $782.33 | $2,648.94 |
| Return | $4.67/$1 | $2.54/$1 | $3.60/$1 |

(The amount of need activated IMPACT-p litter treatment required to treat BLR would be 55 pounds @ $508.75.)

Two separate field trials were run at an integrated poultry complex during July and August 1996. Need activated IMPACT-P litter treatment was applied to the test houses at the recommended rate of one pound per 1,000 square feet. IMPACT-P was spread over floor litter after disinfection procedures using an inexpensive seed spreader. The time required to treat one house was approximately ten minutes.

A.

| Results: | Control | IMPACT-P | Variance |
|---|---|---|---|
| Livability | .9608 | .9657 | .0049 |
| Average Weight | 3.72 | 4.08 | 0.36 |
| Feed Conversion | 1.8889 | 1.7657 | 0.1232 |
| Pay/1,000 Placed | 134.68 | 205.43 | 70.75 |
| Grower Rank | 38/44 | 3/44 | +35 |

The grower used need activated IMPACT-P litter treatment in one of the two houses, the other serving as a control. 20,400 birds were started in each house for a 42 day growout. Settlement pay for the treated house was 52.5% greater and the return on investment in need activated IMPACT-P litter treatment used was $7.80 per $1.00 in IMPACT-P cost. (It must be noted that the control house in this field trial was without feed for a period of 5–6 hours)

B.

| Results: | Control | IMPACT-P | Variance |
|---|---|---|---|
| Livability | .9713 | .9738 | .0049 |
| Average Weight | 3.51 | 3.74 | .23 |
| Feed Conversion | 1.8578 | 1.8038 | .054 |
| Pay/1,000 Placed | 131.44 | 169.81 | 38.37 |
| Grower Rank | 30/36 | 8/36 | +22 |

The grower used need activated IMPACT-P litter treatment in two test houses populated with 40,000 birds for a 43 day growout. Two houses used for control were populated with 30,000 birds. Settlement pay for the IMPACT-P treated IN the 7 FLOCK HISTORIES test there was an improvement over the HISTORIES of 0.24 in the number of living, 0.34 in gain per day, 0.03 in food conversion and 0.48 in integrated cost factor. The improvement in integrated cost factor of the SAME FARM test resulted in a test house improvement versus 7 FLOCK HISTORY of 0.68, and 0.32 as compared to the control house trial.

Preferred bacteria, in addition to those present in need activated IMPACT-P litter treatment, are those beneficial bacteria normally present in poultry particularly the caecum and the ceca. The beneficial bacteria are discussed in the patents previously referred to in the "Background of the Invention". The preferred bacteria are non-pathogenic aerobic bacteria or bacteria that can live in an aerobic environment known as faculative organisms. The bacteria are preferably not cow manure composition made by composting cow manure with thermophilic aerobic bacteria, because there is no control of either the numbers or the identity of the bacteria.

The need activated IMPACT-P litter treatment of the present invention is effective against $E$-$coli$, Salmonella, Campylobacter and many other organisms, including those that cause saculitis.

We claim:

1. A method for improving the yield of poultry in a poultry house comprising
   a) treating poultry litter in the poultry house with a dry composition, the composition comprising one or more bacteria which are non-pathogenic to poultry, and one or more enzymes capable of breaking down poultry manure for digestion by the non-pathogenic bacteria, and a carrier for the non-pathogenic bacteria and the enzymes, the composition being activated by a moisture in poultry droppings to cause rapid growth of the non-pathogenic bacteria thus depriving pathogens from an opportunistic environment, and
   b) introducing poultry into the poultry house.
2. The method of claim 1 wherein the non-pathogenic bacteria is selected from the group consisting of *Bacillus cereus, Bacillus lentimorbius, Bacillus stearothermophilus* and mixtures thereof.
3. The method of claim 1 wherein the enzyme is selected from the group consisting of protease, amylase, lipase and mixtures thereof.
4. The method of claim 1 wherein the carrier is perlite.
5. The method of claim 1 wherein a concentration of the non pathogenic bacteria is greater than $1 \times 10^8$ living bacteria per square foot of litter on the floor of the poultry house.
6. The method of claim 1 wherein a concentration of the non pathogenic bacteria is greater than $1.5 \times 10^9$ living bacteria per square foot of litter on the floor of the poultry house.

7. A method for improving the yield of poultry in direct contact with poultry litter comprising applying to the poultry litter a dry composition containing one or more bacteria which are non-pathogenic to poultry, and one or more enzymes capable of breaking down poultry manure for digestion by the non-pathogenic bacteria, the composition being activated by moisture contained in poultry droppings, introducing and growing poultry directly on the litter, the droppings from the poultry activating the dry composition to cause growth of the non-pathogenic bacteria to the exclusion of pathogens.

8. The method of claim 7 wherein the dry composition is applied before beginning a poultry growout cycle.

9. The method of claim 7 wherein the dry composition is applied only once during a poultry growout cycle.

10. The method of claim 7 wherein the dry composition is applied in a sufficient amount to improve the yield of the poultry.

11. The method of claim 7 wherein a carrier for the non-pathogenic bacteria and the enzymes is present in the dry composition, the carrier having major and minor dimensions each greater than 2 millimeters.

12. The method of claim 7 wherein the non-pathogenic bacteria is selected from the group consisting of *Bacillus cereus, Bacillus lentimorbius, Bacillus stearothermophilus* and mixtures thereof.

13. The method of claim 7 wherein the enzyme is selected from the group consisting of protease, amylase, lipase and mixtures thereof.

14. The method of claim 7 wherein a carrier for the non pathogenic bacteria and the enzymes is present in the dry composition, the carrier being perlite.

* * * * *